United States Patent [19]

Myers et al.

[11] Patent Number: 4,521,194
[45] Date of Patent: Jun. 4, 1985

[54] METHOD FOR REMOVING INCIPIENT CARIOUS LESIONS AND/OR STAIN FROM TEETH

[76] Inventors: William D. Myers, 5855 Wingcroft Ct., Birmingham, Mich. 48010; Terry D. Myers, 25334 Lyncastle La., Farmington Hills, Mich. 48018

[21] Appl. No.: 564,387

[22] Filed: Dec. 22, 1983

[51] Int. Cl.³ .................................................. A61C 5/00
[52] U.S. Cl. ................................... 433/215; 128/303.1
[58] Field of Search ...................... 433/215; 128/303.1, 128/365, 395

[56] References Cited

U.S. PATENT DOCUMENTS 4,273,535  6/1981  Yamamoto et al. ................. 433/215

Primary Examiner—John J. Wilson
Attorney, Agent, or Firm—Gifford, VanOphem, Sheridan, Sprinkle & Nabozny

[57] ABSTRACT

The present invention provides a method for removing incipient carious lesions and/or stain from human teeth. The method of the present invention comprises the steps of aiming a yttrium-aluminum-garnet laser so that its output inpinges upon the lesion and/or stain and thereafter repeatedly activating the laser in pulse mode until the incipient carious lesion and/or stain is removed from the tooth.

3 Claims, 3 Drawing Figures

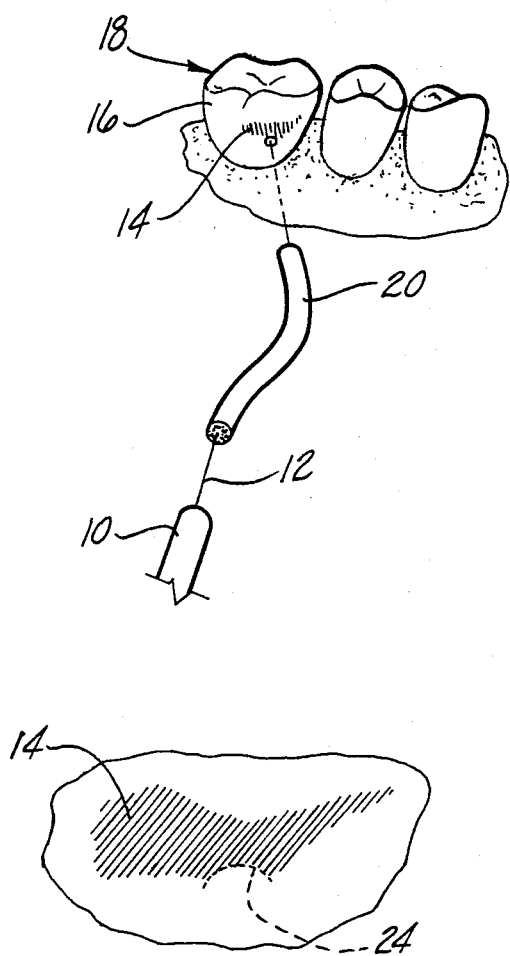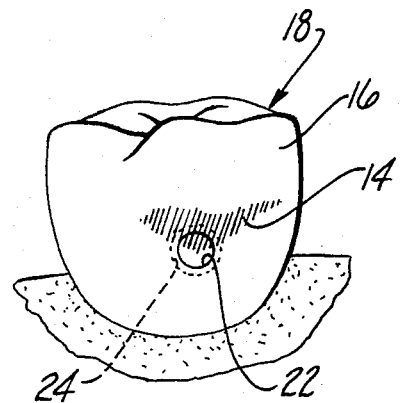

METHOD FOR REMOVING INCIPIENT CARIOUS LESIONS AND/OR STAIN FROM TEETH

BACKGROUND OF THE INVENTION

I. Field of the Invention

The present invention provides a method for removing incipient carious lesions and/or stain from teeth and, more particularly, from human teeth.

II. Description of the Prior Art

Carious lesions or tooth decay are initiated by bacteria which reside in tooth plaque. These bacteria produce acids which diffuse through a matrix of water-protein-lipid and ultimately dissolve the hydroxyapatite crystals which form the tooth enamel.

The dissolution of the enamel hydroxyapatite crystals by the bacteria acid is an intermittent and relatively slow process often extending up to a period of three years before the lesion can be diagnosed clinically by either X-rays or clinical examination. At this point, the carious lesion has invaded the tooth dentin and requires restoration. Such restoration is typically accomplished by drilling and filling the tooth.

Incipient carious lesions are areas of the tooth where the decay can be seen but has not yet broken through the enamel and invaded the dentin. There is no previously known method for removing such incipient decay and/or stain on the enamel surfaces of the tooth although good oral hygiene techniques, such as brushing, and tooth coating slow the tooth decay process. However, once incipient decay is visible on the tooth, the decay will eventually penetrate through the enamel and into the dentin whereupon restoration of the tooth is required.

There have been a number of previously known experiments in which teeth have been subjected to laser irradiation to determine the alteration, if any, of the physical and/or chemical properties of the dental enamel. These studies have shown that the hydroxyapatite crystals that form the enamel fuse somewhat at the surface when lased and renders the enamel more impervious to acids of the type which cause tooth decay. These previous studies, however, have also concluded that the use of a laser to remove tooth decay is ineffective due, in part, to possible damage to the pulp. None of these previously known studies, however, have employed a laser in an attempt to remove incipient carious lesions from the tooth.

SUMMARY OF THE PRESENT INVENTION

The present invention provides a method for removing incipient carious lesions from teeth, including human teeth.

In brief, the method of the present invention comprises the steps of aiming a pulsed laser at the incipient carious lesion and/or stain and thereafter repeatedly activating the laser until the incipient carious lesion and/or stain is eradicated from the tooth. Preferably, the laser is a yttrium-aluminum-garnet laser.

In practice, it has been found that the laser obliterates the incipient carious lesion not only in the area impinged by the laser beam but also in the immediately surrounding areas. Furthermore, it is believed that the laser beam not only removes the incipient carious lesion from the tooth but also slightly fuses the hydroxyapatite crystal which form the enamel on the surface of the tooth. Such fused enamel renders the enamel surfaces more impervious to subsequent decay than the natural state of the tooth.

The precise physical process by which the laser obliterates the incipient carious lesion and/or stain and yet leaves the tooth enamel intact is not entirely understood. However, since incipient carious lesions are softer than enamel, it is believed that the high energy laser beam essentially vaporizes this softer material but is of insufficient energy to obliterate the harder enamel.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 1 is the perspective view illustrating the apparatus employed to carry out the method of the present invention; and FIGS. 2 and 3 are a diagrammatical view illustrating steps of the preferred embodiment of the present invention.

DETAILED DESCRIPTION OF THE PREFERRED EMBODIMENT OF THE INVENTION

With reference first to FIG. 1, an apparatus for carrying out the method of the present invention is thereshown and comprises a laser 10 which, upon activation, generates a laser beam 12. The laser 10 is a pulse laser and preferably is a yttrium-aluminum-garnet laser which produces an energy output of 1-100 millijoules for several picoseconds with a beam diameter of 50-2000 microns.

With reference now to FIGS. 1 and 2, the laser 10 is employed to remove an incipient carious lesion and/or stain 14 formed on the occlusal surface 16 of a tooth 18. The laset output beam 12 is aimed at the lesion 14 through any conventional delivery system 20, such as an optacle fiber bundle.

With reference now to FIGS. 2 and 3, upon activation of the laser 10, the laser eradicates the incipient carious lesion both in the area 22 of the laser beam impingement but also in a relatively small area 24 surrounding the area 22 of the laser beam impingement thus producing the results shown in FIG. 3 in which a portion of the incipient carious lesion 14 is removed from the tooth. Thereafter, the laser 10 is reaimed through the delivery system 20 to the remaining portions of the incipient carious lesion 14 and reactivated until the entire lesion 14 is eradicated from the tooth.

In practice, it has been shown that the use of the pulse laser to remove the lesion 14 effectively removes the lesion 14 without damaging the tooth enamel. Furthermore, studies have shown that the laser beam slightly fuses the crystals which form the tooth enamel and render the tooth enamel more imprevious to decay than in its normal unlased state.

Having described our invention, however, many modifications thereto will become apparent to those skilled in the art to which it pertains without deviation from the spirit of the invention as defined by the scope of the appended claims.

We claim:

1. A method for removing an incipient carious lesion and/or stain from a tooth comprising the steps of:

aiming a pulsed laser so that the output from the laser impinges upon the incipient carious lesion and/or stain, repeatedly activating the laser until the incipient carious lesion and/or stain is removed from the tooth, wherein said laser has a power output in the range of one to one hundred millijoules cm$^2$, a beam diameter of substantially 50–2000 microns and a pulse duration of several picosecond.

2. The invention as defined in claim 1 wherein said laser is a yttrium-aluminum-garnet laser.

3. The invention as defined in claim 1 wherein said aiming step further comprises the step of passing the laser beam through an optical delivery system.

* * * * *